US012796904B2

(12) United States Patent
Kumar

(10) Patent No.: US 12,796,904 B2
(45) Date of Patent: Nov. 17, 2026

(54) VIDEO LARYNGOSCOPE

(71) Applicant: Sujit Kumar, Redmond, WA (US)

(72) Inventor: Sujit Kumar, Redmond, WA (US)

( * ) Notice: Subject to any disclaimer, the term of this patent is extended or adjusted under 35 U.S.C. 154(b) by 107 days.

(21) Appl. No.: 18/908,056

(22) Filed: Oct. 7, 2024

(65) Prior Publication Data

US 2025/0113987 A1 Apr. 10, 2025

Related U.S. Application Data

(60) Provisional application No. 63/543,039, filed on Oct. 6, 2023.

(51) Int. Cl.

| | |
|---|---|
| ***A61B 1/267*** | (2006.01) |
| ***A61B 1/00*** | (2006.01) |
| ***A61B 1/05*** | (2006.01) |
| ***A61B 1/06*** | (2006.01) |

(52) U.S. Cl.

CPC ............ *A61B 1/267* (2013.01); *A61B 1/0004* (2022.02); *A61B 1/00048* (2013.01); *A61B 1/00052* (2013.01); *A61B 1/00096* (2013.01); *A61B 1/00105* (2013.01); *A61B 1/00124* (2013.01); *A61B 1/00128* (2013.01); *A61B 1/0014* (2013.01); *A61B 1/00144* (2013.01); *A61B 1/05* (2013.01); *A61B 1/0676* (2013.01)

(58) Field of Classification Search
None
See application file for complete search history.

(56) References Cited

U.S. PATENT DOCUMENTS

| | | | | |
|---|---|---|---|---|
| 2012/0116388 | A1* | 5/2012 | Houser .......... | A61B 17/320092 606/1 |
| 2021/0338052 | A1* | 11/2021 | Ouyang ............ | A61B 1/00128 |
| 2022/0142708 | A1* | 5/2022 | Melsky ............. | A61B 1/00181 |
| 2023/0397795 | A1* | 12/2023 | Pilbeam ................ | A61B 1/045 |
| 2024/0074644 | A1* | 3/2024 | Tjell ....................... | A61B 1/05 |

* cited by examiner

*Primary Examiner* — Tessa M Matthews
(74) *Attorney, Agent, or Firm* — Vani Moodley, Esq.

(57) ABSTRACT

The present invention provides a video laryngoscope (100) to perform the intubation process. The video laryngoscope (100) includes a handle (10), a blade (20), a display unit (30), and an attachment assembly (25). The handle (10) includes a camera housing (16) with an image sensor (161) and a light source (162) arranged therein. The image sensor (161) is attached to the handle (10) through a camera channel (15) to visualise the path of the endotracheal tube. The camera housing (16) has a deflector (18) to avoid the blurry and distorted visuals generated due to the scattering of the light from the light source (162). The blade (20) is arranged on the handle (10) to cover the handle (10) and the camera channel (15). Further, the display unit (30) is provided for better visibility of the display screen (34) to visualise the path of the endotracheal tube.

18 Claims, 8 Drawing Sheets

VIDEO LARYNGOSCOPE

TECHNICAL FIELD

The present invention relates to a laryngoscopy device. More particularly, the present invention relates to a video laryngoscope.

BACKGROUND

A laryngoscope is a device, typically comprising a handle and a blade, which is used by clinicians during endotracheal intubation. The laryngoscope assists with intubation by allowing the clinician to visualise the path of the endotracheal tube as the laryngoscope passes through the glottis towards the trachea.

Intubation is the process of inserting a tube, called an endotracheal tube, through the mouth and then into the airway. Intubation is a necessary procedure performed before any surgery that requires a patient to be placed under general anaesthesia. Intubation is also performed on patients who need to be placed on a ventilator to assist with breathing. The endotracheal tube is connected to either an anaesthesia system or a ventilator, that pushes air into the lungs to deliver a breath to the patient. The laryngoscope is the device used for intubation.

Presently, traditional video laryngoscopes come in two form factors. In the first form factor, the display is detached from the handle and is attached to a cart. The display attached to the cart has a limited manoeuvrability. Also, the size of the display is 7-11 inches and the carts are bulky and hard to move around. While performing the intubation process, the clinician needs to look away from the patient and towards the display which is attached to the cart and not looking at the patient increases the risk of a failed process. In addition, cart-based systems tend to be more expensive and hospitals purchase a few units to be shared between multiple operating rooms. This results in the video laryngoscope not being available for every intubation procedure. In the second form factor, the display is attached to the handle but the displays are small, have poor image quality and are not manoeuvrable. Both form factors result in increased risk to the patient and repeated intubations.

Further, traditional video laryngoscope includes reusable blades that are used again and again for the intubation process. Repeated use of the blades leads to a higher risk of infection, increased operational burden on hospitals and high ownership costs.

Therefore, there is a need for a video laryngoscope, which overcomes few or all drawbacks of the prior art.

STATEMENT OF THE INVENTION

According to the present aspect of the invention, there is provided a video laryngoscope that may provide enhanced visualization during intubation procedures. The video laryngoscope may include a handle for improved grip, facilitating ease of use during intubation. At the lower end of the handle, a camera housing can be arranged, which may incorporate an image sensor and a light source. A deflector may be positioned between the image sensor and the light source to minimize light scatter and improve image quality during the procedure.

The video laryngoscope may further comprise a display unit that can be removably attached to the handle via a hinge mechanism, enabling adjustable viewing angles during use. The display unit may also be connected to the handle through an attachment assembly that includes a quick-connect and release mechanism. This mechanism can be facilitated by radially biased ball projections, allowing for secure attachment and easy detachment. Additionally, the display unit may be adapted to automatically adjust the orientation of the displayed image when rotated, ensuring clear viewing from various procedural positions.

In one embodiment, the deflector may be detachable and replaceable, allowing for maintenance or replacement as needed. The display unit may also include a user-accessible record button, enabling the clinician to capture images and videos during the intubation process.

The attachment assembly of the display unit and handle may integrate automatic electrical connectivity upon attachment. Specifically, electrical connectors within the attachment assembly can automatically establish a connection once the display unit is aligned and attached to the handle. This feature allows for instantaneous visual feedback on the display screen. The display unit may further include an output port to connect external displays for broader viewing access, especially in teaching environments or complex procedures.

In another aspect, the ball projections within the attachment assembly may be mechanically biased to extend and retract, ensuring the secure attachment of the display unit while facilitating easy detachment when necessary. For enhanced sterility during the procedure, the laryngoscope may be equipped with a disposable cover that wraps around both the display unit and the attachment assembly, maintaining a sterile environment throughout intubation.

The handle of the video laryngoscope may also feature a dual ball mechanism to enable secure and quickly detachable connections for various blade types. The laryngoscope may support different blade geometries for adults and children, enhancing its versatility in medical procedures.

The display unit may include a touchscreen interface, enabling interactive control over device settings, access to stored data, and adjustments to operational parameters. Additionally, the display unit may feature an automatic image orientation correction function that can adjust the displayed image to a standard upright orientation when the display is rotated by approximately 180 degrees. This functionality is particularly useful during procedures involving patients with elevated body mass index, where different viewing angles are necessary.

In certain embodiments, the image orientation correction feature may be activated by user input, such as swiping gestures on the display screen or pressing a designated button. The display unit may also have a rotation mechanism capable of 360-degree movement, with predetermined stop positions at specific angles for optimal viewing. The automatic image orientation correction feature may ensure proper display alignment at each stop.

Furthermore, the display unit may offer password-protected access to stored visual data, which requires a user-defined password to access saved video files or connect to external computing devices like personal computers, tablets, or other similar devices. The password protection feature may further enhance data security, safeguarding patient information. The video laryngoscope may include a default password that can be configured by the user to a six-digit combination, ensuring flexible but secure access to sensitive data.

The invention may also provide encryption and password protection features to secure the connectivity of the video laryngoscope, preventing unauthorized access or data transfer during or after intubation procedures.

In one embodiment, the laryngoscope may include an integrated visual transmission capability through a camera channel. The camera housing within the channel can include a light source and an image sensor, separated by a light-absorbing deflector to reduce glare. The display unit may be attached to the handle via a hinge, which allows it to rotate and provide optimal viewing angles. The connection system between the handle and the display unit may also include a housing with electrical connectors to enable instant visual feedback on the display.

An object of the present invention is to provide a video laryngoscope.

Another object of the present invention is to provide a video laryngoscope, which is adapted to control the infection rate in hospitals.

Yet another object of the present invention is to provide a video laryngoscope which is adapted to capture clear and non-distorted images of the path of the endotracheal tube, larynx, trachea or airway.

Still another object of the present invention is to provide a video laryngoscope which provides better visibility of the path of the endotracheal tube to the clinicians.

BRIEF DESCRIPTION OF THE DRAWINGS

Other features and advantages of the invention will become apparent when reading the detailed description given below, purely by way of example and in a non-limitative manner, referring to the following figures.

DETAILED DESCRIPTION

An embodiment of this invention, illustrating its features, will now be described in detail. The words "comprising, "having, "containing," and "including," and other forms thereof, are intended to be equivalent in meaning and be open ended in that an item or items following any one of these words is not meant to be an exhaustive listing of such item or items, or meant to be limited to only the listed item or items.

The present invention provides a video laryngoscope. The video laryngoscope is adapted to seamlessly attach and detach a display unit and a blade from a handle. The video laryngoscope is adapted to avoid the blurry and distorted visuals of the path of the endotracheal tube. Further, the video laryngoscope is adapted to control the infection rate, which could spread due to the regular laryngoscopes. Furthermore, the video laryngoscope allows the clinicians to perform the intubation process without sacrificing the visibility of the display unit.

The terms "first," "second," and the like, herein do not denote any order, quantity, or importance, but rather are used to distinguish one element from another, and the terms "an" and "a" herein do not denote a limitation of quantity, but rather denote the presence of at least one of the referenced item. The disclosed embodiments are merely exemplary of the invention, which may be embodied in various forms.

Figure 1:
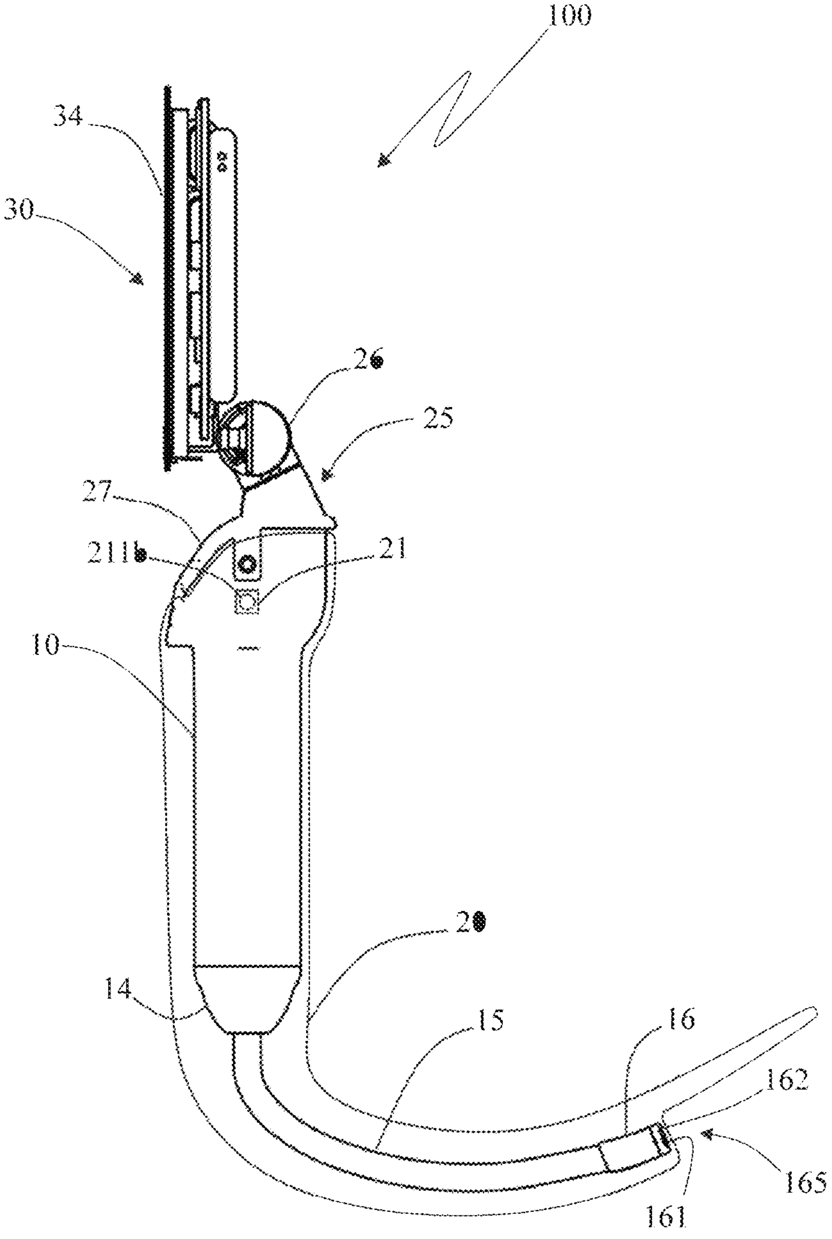
FIG. 1 illustrates a side view of a video laryngoscope in accordance with the present invention.
Figure 2A:
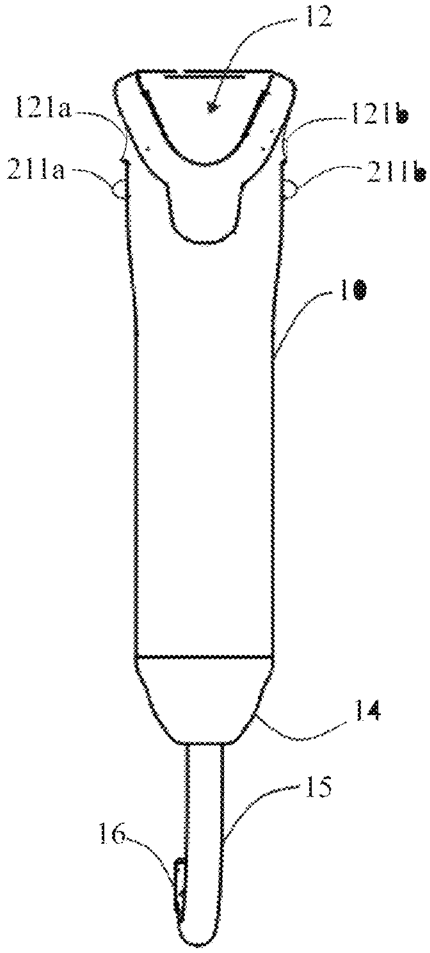
FIG. 2*a*-2*b* illustrate a front view and a top view of a handle of the video laryngoscope in accordance with the present invention.
Figure 2B:
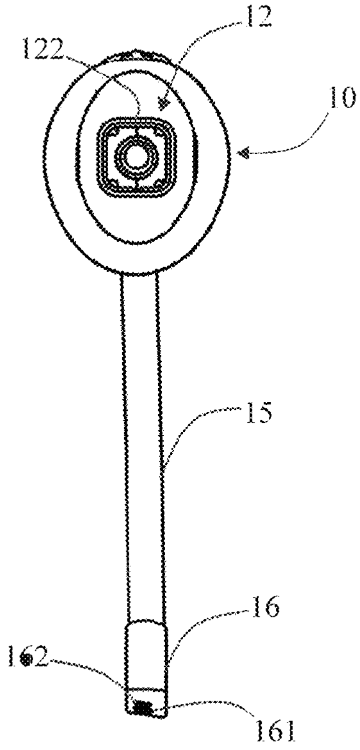

Referring now to FIGS. 1, 2*a*, and 2*b*, a video laryngoscope (100) in accordance with the present invention is illustrated. The video laryngoscope (100) includes a handle (10), a blade (20), a display unit (30), and an attachment assembly (25) to attach the display unit (30) to the handle (10). The handle (10) is an elongated member that has an ergonomic design that allows clinicians to easily hold the handle (10) during an intubation process. The handle (10) has an upper end and a lower end. The upper end of the handle (10) is provided with a receiving port (12) to receive the attachment assembly (25).

The lower end of the handle (10) is provided with a tapered portion (14). Specifically, the lower end of the handle (10) is provided with a camera channel (15) that extends from the tapered portion (14) of the handle (10). The camera channel (15) is a flexible link extending from the tapered portion (14) of the handle (10) and comprises an electric circuit to transfer the visuals such as images and videos to the receiving port (12). Specifically, the camera channel (15) is electrically connected to a first terminal (122) of the receiving port (12). The camera channel (15) has a first end connected to the tapered portion (14) of the handle (10) and a second end comprising a camera housing (16). The camera housing (16) of the camera channel (15) is provided to capture visuals of the path of the endotracheal tube, larynx, trachea or airway.

Figure 3:
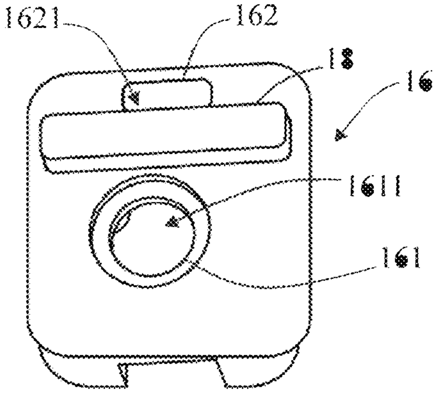
FIG. 3 illustrates a perspective view of a camera housing of the video laryngoscope in accordance with the present invention.

Referring now to FIGS. 1, and 3, the camera housing (16) comprises an image sensor (161) and a light source (162). The image sensor (161) facilitates capturing of the visuals of the path of the endotracheal tube, larynx, trachea or airway. Specifically, an image sensor opening (1611) in the camera housing (16) allows the image sensor (161) to capture the visuals of the path of the endotracheal tube, larynx, trachea or airway. In the present aspect of the invention, the image sensor (161) is a 2-megapixel (MP) camera, but a person skilled in the art can use any other image sensor (161) having different specifications. For example, a person skilled in the art can configure the image sensor to meet different specifications, such as higher resolution sensors (e.g., 5 MP or 10 MP) for more detailed imaging. The image sensor may also include options for adjusting image brightness, contrast, and zoom functionality for a better visual of the intubation path.

Further, the camera housing (16) includes a light source opening (1621) to allow the light source (162) to illuminate the path of the endotracheal tube and the airway. Furthermore, the camera housing (16) has a deflector (18). Specifically, the deflector (18) is arranged on an outer surface of the camera housing (16) separating the image sensor opening (1611) and the light source opening (1621). The deflector (18) avoids the direct exposure of the light source (162) to the image sensor (161). The light source (162) is configured to provide focused illumination of the path of the endotracheal tube, larynx, and trachea. It can be configured to emit varying intensities of light, depending on the clinical environment or patient anatomy. In particular, the light source is adjustable to illuminate dark or obscured areas, ensuring clear visibility during the intubation process.

Figure 4:
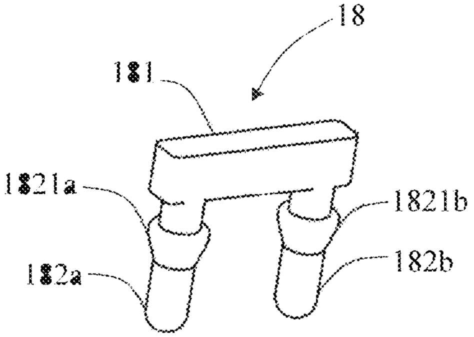
FIG. 4 illustrates a perspective view of a deflector of the video laryngoscope in accordance with the present invention.

In the present aspect of the invention, the deflector (18) is a rectangular strip as shown in FIG. 4. The rectangular strip is made up of a silicone material. A person skilled in the art can configure the deflector (18) with any other material, shape or size according to the size and position of the image sensor (161) and the light source (162). The deflector (18) is horizontally arranged between the light source opening (1621) and the image sensor opening (1611) to avoid the scattering of the light on the image sensor (161). Specifically, the deflector (18) is positioned between the light source (162) and the image sensor (161) to minimize light scattering that can obscure or distort the visuals captured by the image sensor (161). The deflector (18) is made from a silicone material, known for its light-absorbing properties, but other light-absorbing materials (e.g., polycarbonate or specialized plastic) can also be used. This ensures that the captured images are sharp and free from glare or halos that could obscure the clinician's view.

Referring now to FIGS. 3, and 4, the deflector (18) includes a rectangular portion (181), and two legs (182*a*, 182*b*) extending from the ends of the rectangular portion (181). The two legs (182*a*, 182*b*) are provided with respective locking elements (1821*a*, 1821*b*) to attach the deflector (18) to the camera housing (16). Specifically, the camera housing (16) has two openings (not shown) to receive the locking elements (1821*a*, 1821*b*) of the two legs (182*a*, 182*b*) to hold the deflector (18) on the outer surface of the camera housing (16). The deflector (18) is fixedly attached to the camera housing (16) using the locking elements (1821*a*, 1821*b*) but a person skilled in the art can provide the deflector (18) which is detachable from the camera housing (16). Specifically, the deflector (18) is detachable from the camera housing (16) if the deflector (18) has incurred damage or requires replacement.

In another aspect of the invention, the deflector (18) is an extruded portion (not shown) that extends from the outer surface of the camera housing (16). The extruded portion is provided between the image sensor opening (1611) and the light source opening (1621) to avoid direct light exposure to the image sensor (161) from the light source (162). The scattering of the light from the light source (162) makes images distorted and blurry. The deflector (18) avoids direct exposure of the light source (162) to the image sensor (161) to avoid distortion and blurriness of the images.

In another aspect of the invention, the deflector (18) is a thin sheet arranged between the image sensor opening (1611) and the light source opening (1621). The sheet can be made up of any material that absorbs light to avoid the direct exposure of the light source (162) on the image sensor (161).

Figure 5:
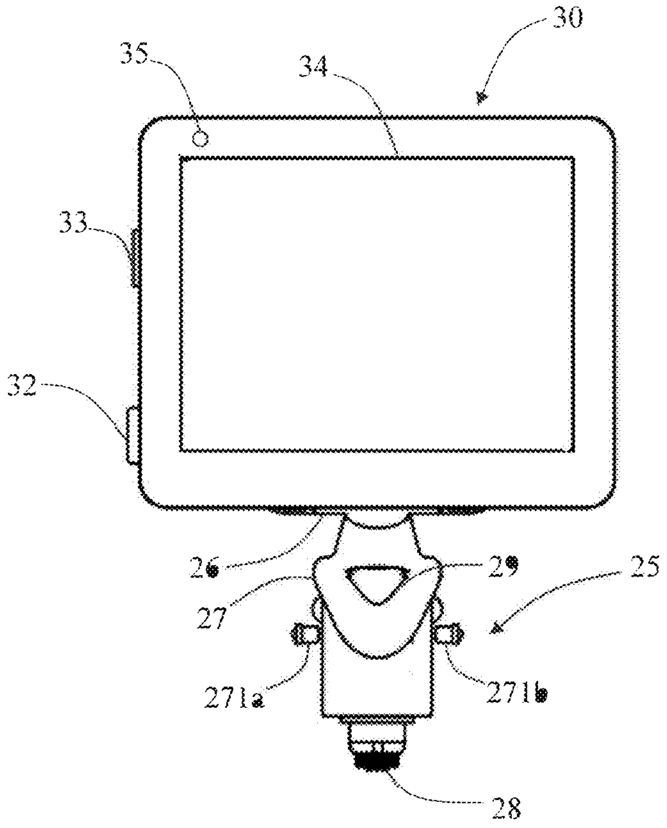
FIG. 5 illustrates a front view of a display assembly of the video laryngoscope in accordance with the present invention.

Referring now to FIGS. 1, and 5, the display unit (30) is provided which is attachable to the handle (10) through the attachment assembly (25). The attachment assembly (25) includes a housing (27), and a second terminal (28) which is electrically connected to the display unit (30). The housing (27) is connected to the display unit (30) using a hinge (26). The hinge (26) is provided to pivot the display unit (30) in a back-and-forth direction. The hinge (26) is connected to the display unit (30) and the housing (27). Specifically, the hinge (26) has a connecting element (not shown) that is adapted to attach to the housing (27). The housing (27) receives the connecting element of the hinge (26) to allow the display unit (30) to freely rotate around the central axis of the handle (10). The hinge (26) allows the display unit (30) to rotate in all the possible directions to configure the display unit (30) in a required position to provide better visibility to the clinician. The hinge (26) that connects the display unit (30) to the handle (10) allows 360-degree rotation, but it also includes pre-determined stops at angles such as 45, 90, 180, and 270 degrees. These stop points are built into the hinge mechanism, ensuring that the display unit locks into position at these angles. This helps the clinician maintain a stable and optimal view of the airway during intubation, without requiring manual adjustments. The automatic image adjustment ensures that the image remains properly oriented regardless of the display unit's rotation.

Further, the housing (27) includes two ball projections (271*a*, 271*b*) extending from an outer surface of the housing (27) and arranged opposite to each other to securely attach and detach the housing (27) to the handle (10). The two ball projections (271*a*, 271*b*) are biased to radially extend away from the centre axis of the housing (27). The housing (271*a*, 271*b*) is attached to the receiving port (12) of the handle (10). Specifically, the receiving port (12) has two openings (121*a*, 121*b*) to receive the respective ball projections (271*a*, 271*b*) of the housing (27) to securely hold the housing (27) within the receiving port (12) of the handle (10). The two ball projections (271*a*, 271*b*) ensure that the housing (27) is held in place until the two ball projections (271*a*, 271*b*) are pressed to detach the housing (27) of the attachment assembly (25). Specifically, the two ball projections (271*a*, 271*b*) have respective balls arranged at the extreme ends to easily press the two ball projections (271*a*, 271*b*) while detaching the housing (27) from the handle (10). The two ball projections (271*a*, 271*b*) are located on opposite sides of the housing (27). These ball projections are mechanically biased to extend radially outward from the housing (27) and engage with corresponding sockets in the receiving port (12) of the handle (10). This engagement ensures a secure attachment, while pressing the ball projections inward allows for quick detachment of the display unit (30). The ball projections are designed to operate with minimal force, allowing the clinician to quickly adjust or remove the display unit during an intubation procedure Once the display unit (30) is attached to the handle (10) through the attachment assembly (25), the second terminal (28) of the attachment assembly (25) electrically connects with the first terminal (122) of the receiving port (12) of the handle (10) to establish the electric connection between the camera channel (15) and the display unit (30). Specifically, upon attaching the attachment assembly (25) to the handle (10), the first terminal (122) and the second terminal (28) immediately establish an electric connection between the image sensor (161) and the display unit (30) enabling the instantaneous display of visuals of the path of the endotracheal tube, larynx, trachea, or airway on the display screen (34).

Figure 7A:
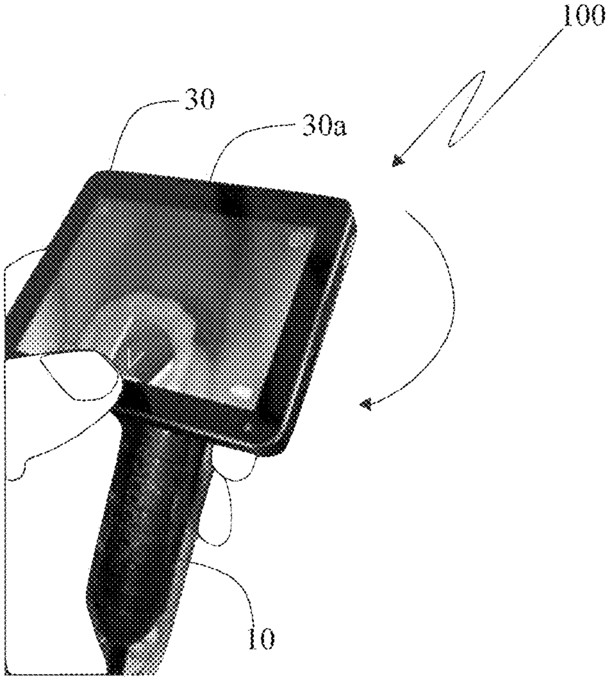
FIG. 7*a*-7*b* illustrates an image orientation correction feature of the display unit in accordance with the present invention.
Figure 7B:
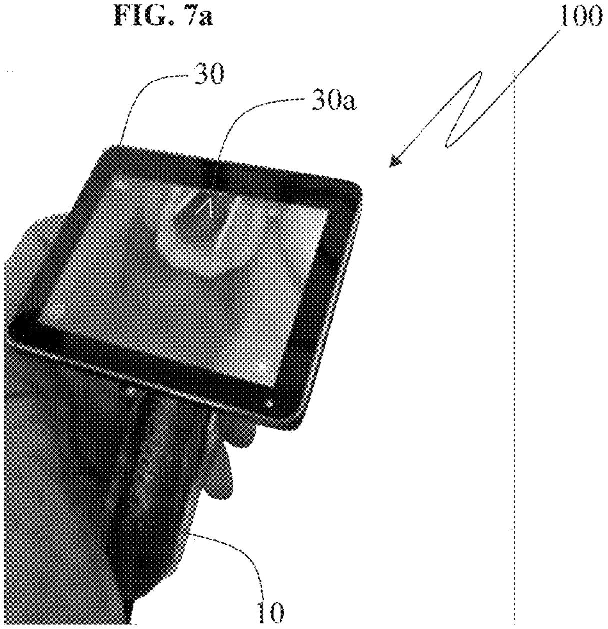

Furthermore, the attachment assembly (25) includes a record button (29) (as shown in FIG. 5) to capture an image or record a video. In the present aspect of the invention, the record button (29) is arranged on a portion of the housing (27). However, a person skilled in the art can arrange the record button (29) on any other portion in such a way that the clinician's thumb easily reaches to the record button (29) to capture an image or record a video. The display unit (30) further includes an automatic image orientation correction feature (30*a*) as shown in FIGS. 7*a*-7*b*. When the display unit (30) is rotated downwards or upwards by approximately 180 degrees or other angles, the image on the display screen (34) automatically adjusts to ensure proper alignment for the clinician. This is particularly beneficial in procedures involving high-BMI patients, where the rotated display ensures better visibility and access to the airway.

Referring now to FIGS. 1, 3, and 5, the display unit (30) includes a battery (not shown), a power button (32), an output port (33), a display screen (34), a touch user interface (TUI) (not shown), a processor (not shown), and a memory (not shown) to store the visuals of the path of the endotracheal tube, larynx, trachea or airway. The battery is arranged within the display unit (30) to supply power to the display screen (34), the image sensor (161) and the light source (162). The battery can be a replaceable battery or a rechargeable battery.

In another aspect of the invention, the handle (10) includes a battery (not shown) that can be used to supply power to the image sensor (161) and the light sensor (162) when the display unit (30) is not attached to the handle (10). In such case, the handle (10) establishes a wireless connection with the display unit (30) or an external display (not shown) to transfer the visuals of the path of the endotracheal tube, larynx, trachea or airway from the image sensor (161) to the display unit (30) or the external display.

The power button (32) is provided on any of the sides of the display unit (30). The power button (32) is within the range of the clinician's fingers. In the present aspect of the invention, the power button (32) is arranged at the bottom left of the display unit (30). The power button (32) is used to power on or power off the display screen (34). Specifically, the power button (32) is pressed and released to power on the display screen (34), and the power button (32) is pressed and held for 3-4 seconds to power off the display screen (34). A person skilled in the art can configure the duration for holding the power button (32) to power off the display screen (34). In the present aspect, the power button (32), is located at the bottom left of the display unit (30). A short press activates the display screen (34), image sensor (161), and light source (162), while a longer press (3-4 seconds) powers down the unit. This minimizes accidental shutdowns and ensures that the display is operational when needed. The record button (29) on the housing further allows clinicians to capture visuals during the procedure, with the captured data automatically saved in a secure, password-protected folder.

In another aspect of the invention, the display screen (34) starts displaying the visuals of the path of the endotracheal tube once the display unit (30) is attached to the handle (10) and the display screen (34) is powered ON using the power button (32). The display screen (34) automatically starts displaying the visual of the endotracheal tube without pressing the record button (29).

In one more aspect of the invention, the video laryngoscope (100) is adapted to start displaying the visuals on the display screen (34) even if the display unit (30) is not attached to the handle (10). The display screen (34) displays the visuals by establishing the wireless connection between the handle (10) and the display unit (30).

Further, the output port (33) is provided on any of the sides of the display unit (30) to connect the display unit (30) to an external display (not shown) to show the visuals of the path of the endotracheal tube. The external display has a bigger screen size than the display screen (34) of the display unit (30). It is obvious to a person skilled in the art to provide a plurality of output ports on the display unit (30).

The display screen (34) of the display unit (30) is adapted to show visuals of the path of the endotracheal tube received from the image sensor (161). In the present aspect of the invention, the display unit (30) has a rectangular shape to accommodate the display screen (34). The display screen (34) has a size of 3.5 inches to provide better visibility from all angles. It is obvious to a person skilled in the art to increase the size of the display screen (34) according to the requirement.

Further, the touch user interface is provided to allow the clinician to interact with the video laryngoscope (100). The touch user interface of the display screen (34) is adapted to review and manage previously recorded images or videos which are stored in the memory of the display unit (30). The touch user interface includes a home page to show the current time and date, a menu icon to access the plurality of icons, and a battery icon to indicate the level of the battery. The display screen (34) is powered on using the power button (32) to display the home page. In the present aspect, the touch user interface (TUI) of the display screen (34) allows the clinician to manually activate the image orientation correction feature (30*a*) as shown in FIGS. 7*a* and 7*b*. The image orientation can be flipped by swiping up on the display screen (34) or by pressing a dedicated 'flip' button on the display unit (30). The clinician interacts with the menu icon of the home page by touching the menu icon displayed on the display screen (34) to access the plurality of the icons. The menu icon is provided on the bottom left corner of the display screen (34) to allow the clinician to reach the menu icon with one hand. After touching the menu icon, the processor receives the touch input from the touch user interface and processes the command to show the plurality of icons on the display screen (34).

Figure 8A:
FIG. 8*a*-8*b* illustrates a security mechanism feature of the video laryngoscope in accordance with the present invention.
Figure 8B:

Further, the video laryngoscope (100) includes a security mechanism (30*b*) for stored visual data, such as images and videos captured during the intubation process as shown in FIGS. 8*a* and 8*b*. Accessing the stored data on the display unit (30) requires a password, which can be user-defined. The default password is '000000,' but it can be configured to any six-digit combination by the clinician to enhance patient data security. The touchscreen interface on the display unit (30) provides intuitive navigation of the device's settings and stored data. Clinicians can interact with the touch user interface (TUI) using simple gestures, such as swiping or tapping icons, to adjust brightness, access stored images, or activate the image orientation correction feature. The display screen (34) is also designed to remain responsive even when the clinician is wearing medical gloves, ensuring seamless operation. The display unit (30) further includes the security mechanism (30*b*) like an encryption system that protects data during transfer to external devices, such as PCs, tablets, or other computing resources as shown in FIGS. 8*a* and 8*b*. A password is required not only for accessing the stored data but also for connecting the video laryngoscope to external computing resources, ensuring that sensitive medical data remains secure. The encryption extends to data transfer, ensuring that files sent to external devices such as PCs or tablets are protected by encryption protocols such as AES-256. This level of encryption ensures compliance with healthcare data security standards.

The plurality of icons is assigned with specific actions to perform after receiving the command from the processor of the display unit (30). Specifically, the plurality of icons includes a settings icon to make changes in the brightness of the display screen, the volume of the sound, turn on or turn off the output port (33), and the like. Further, the plurality of icons includes a photo icon to view and manage previously recorded images, and a video icon to view and manage previously recorded videos. In another aspect of the invention, the plurality of icons includes a folder icon to view and manage the previously recorded images and videos in one place. A person skilled in the art can add more icons to the plurality of the icons to provide additional features and functions.

The touch user interface is adapted to show an indication of the captured image on the display screen (34) when the record button (29) is pressed by the clinician to capture the image. Further, the touch user interface is adapted to show a timer of the recording on the display screen (34) when the record button (29) is pressed and held to record the video. Further, the timer disappears from the display screen (34) after pressing the record button (29) to stop the recording.

In another aspect of the present invention, the display unit (30) includes a charging light (35) to indicate the charging status of the battery. The charging light (35) turns on when the battery is connected to a power source to recharge the battery, and turns off when the battery is not connected to the power source for recharging. It is obvious to a person skilled in the art to arrange the charging light (35) in any of the corners of the display unit (30).

Figure 6:
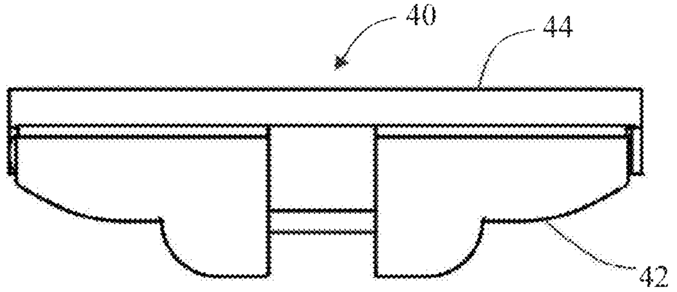
FIG. 6 illustrates a bottom view of a display cover of the video laryngoscope in accordance with the present invention.

Referring now to FIGS. 1, 5 and 6, a display cover (40) is provided to prevent the display unit (30) and the attachment assembly (25) from getting infected during the intubation process. The display cover (40) is made up of a transparent material to allow the clinician to view the display screen (34) without any hindrance. The display cover (40) includes a lower panel (42) and an upper panel (44) hinged at a hinge point. The lower panel (42) and the upper panel (44) pivot around the hinge point to cover the display unit (30). The upper panel (44) and the lower panel (42) of the display cover (40) are pressed to snap fit with each other after placing the display unit (30) within a cavity of the display cover (40). Further, the upper panel (44) has a flexible sheath (not shown) extending from the free end of the upper panel (44) to cover the attachment assembly (25) and a portion of the handle (10). The display cover (40) is disposable and can be disposed of once the intubation process is finished.

Referring again to FIGS. 1, and 2, the handle (10) is adapted to receive the blade (20) from the lower end of the handle (10). The blade (20) is received around the outer surface of the handle (10) to entirely cover the handle (10) and the camera channel (15). The blade (20) is attached to the handle (10) while performing the intubation process. The handle is adapted to receive all types of blades like Macintosh, and Miller. Further, the handle (10) is adapted to receive both adult blades and child blades. The camera channel (15) is adapted to receive all types of blades like Macintosh, and Miller for both adults and children. The handle (10) does not require any other adjustments or mountings to receive adult blades and child blades. The blade (20) is slidable over the camera channel (15) to attach with the handle (10) to perform the intubation process. The blade (20) is detachably attached to the handle (10) and is detachable from the handle (10) after the intubation process.

In the present aspect of the invention, the blade (20) is attachable to the handle (10) through an attachment mechanism (21) of the handle (10). The attachment mechanism (21) includes two ball projections (211*a*, 211*b*) arranged opposite to each other to securely attach and detach the blade (20) to the handle (10). The two ball projections (211*a*, 211*b*) are biased to radially extend away from the centre axis of the handle (10). The two ball projections (211*a*, 211*b*) engage with the blade (20). Specifically, the blade (20) has two openings (not shown) to engage with two ball projections (211*a*, 211*b*) of the handle (10) to securely hold the blade (20) thereover. The two ball projections (211*a*, 211*b*) ensure that the blade (20) is held in place until the two ball projections (211*a*, 211*b*) are pressed to detach the blade (20). The blade (20) is disposed of after detaching from the handle (10) to reduce the chance of infection and cross-contamination. Disposing of the blade (20) after one use allows the video laryngoscope (100) to control the spread of infection which can be spread by using the same blade again and again.

Further, the blade (20) has a camera housing opening (165) to allow the image sensor (161) and the light source (162) to capture the visuals of the path of the endotracheal tube. The image sensor (161) captures the visuals of the path of the endotracheal tube, larynx, trachea or airway and transfers the visuals to the display unit (30).

Before performing the intubation process, the clinicians attach the blade (20) to the handle (10). The blade (20) can be an adult blade or a child blade. The blade (20) is slidable over the camera channel (15) and is attached to the handle (10) through the attachment mechanism (21) of the handle (10).

Figure 9A:
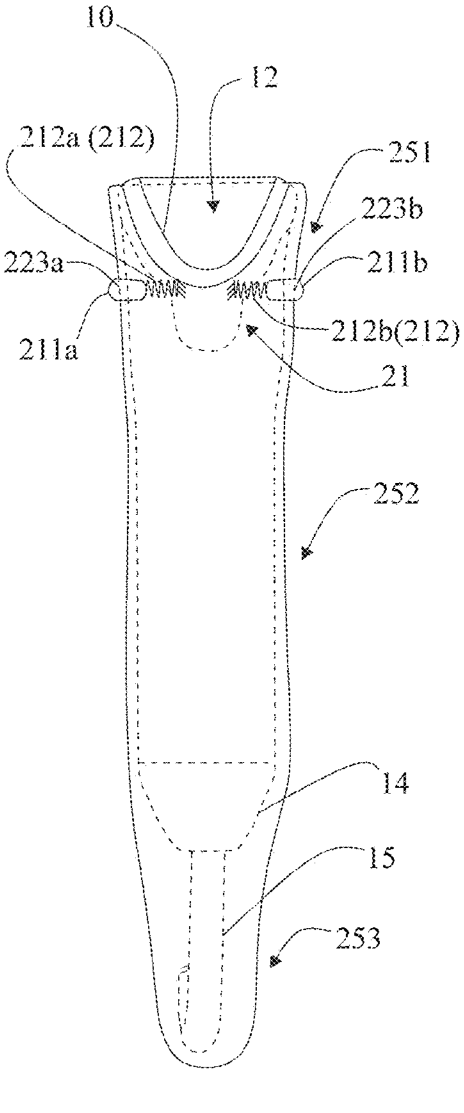
FIG. 9*a*-9*c* illustrate a front view of the handle while detaching a blade in accordance with the present invention.
Figure 9B:
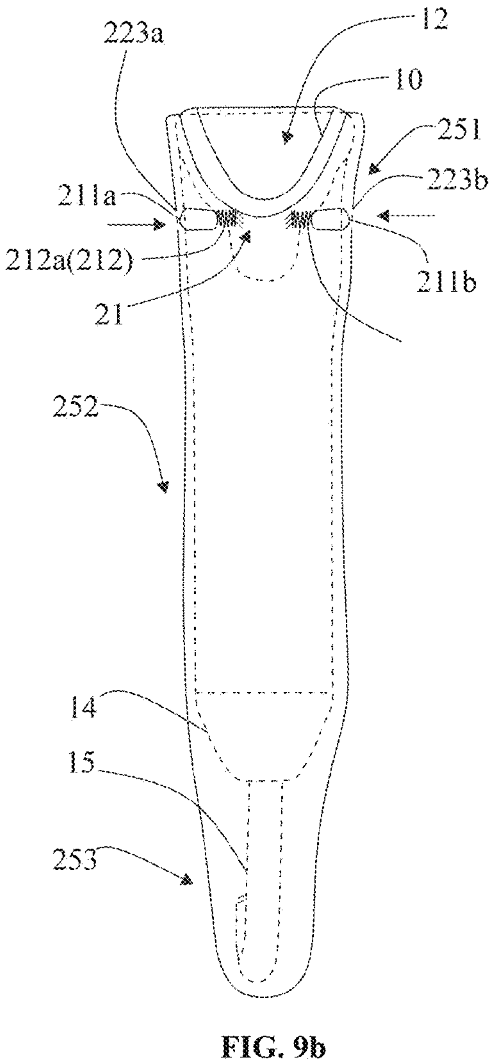
Figure 9C:
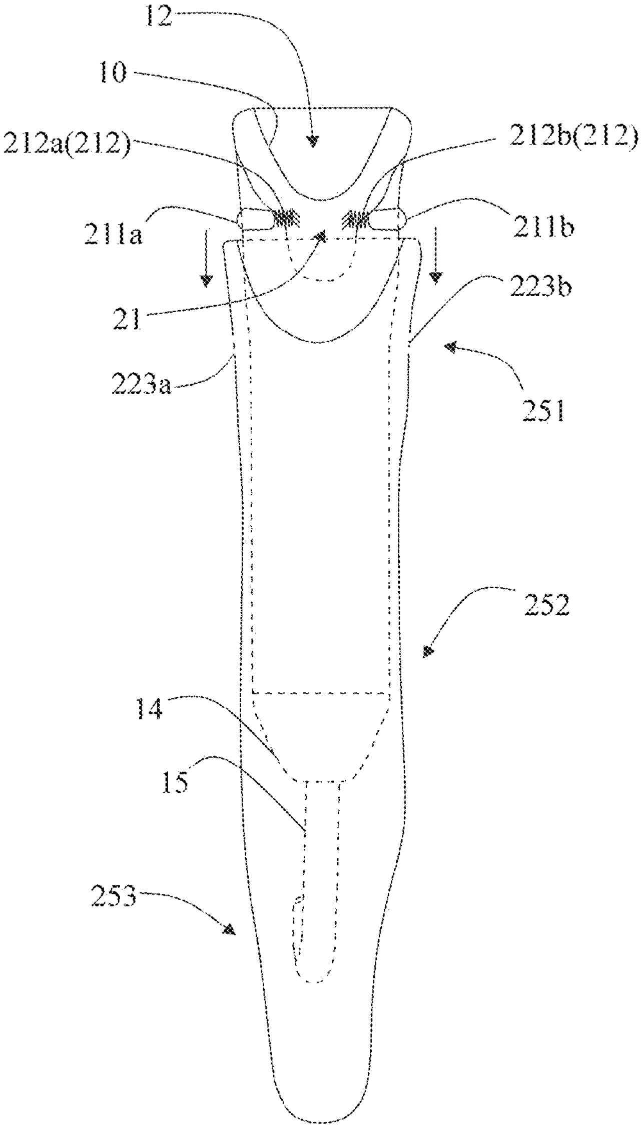

Referring now to FIGS. 9*a*-9*c*, in the present embodiment of the invention, the blade (20) is attachable to the handle (10) through an attachment mechanism (21) of the handle (10). The attachment mechanism (21) includes at least two ball projections (211*a*, 211*b*) arranged opposite to each other to securely attach and detach the blade (20) to the handle (10). The two ball projections (211*a*, 211*b*) are biased to radially extend away from the centre axis of the handle (10). The two ball projections (211*a*, 211*b*) are configured to engage with the blade (20). Specifically, the two ball projections (211*a*, 211*b*) are biased to extend radially outward from the center of the handle (10) using a biasing member (212) such as springs. The biasing member (212) is positioned inside the handle (10) and applies a continuous force to the ball projections (211*a*, 211*b*), to configure an extended position of two ball projections (211*a*, 211*b*) during the attachment of the blade (20). The two ball projections (211*a*, 211*b*) have corresponding biasing members (212*a*, 212*b*) to bias the two ball projections (211*a*, 211*b*) away from the handle (10) to engage and hold the blade (20) in an attached position. When the blade (20) is attached, the ball projections (211*a*, 211*b*) engage with corresponding 122 (223*a*, 223*b*) in the blade (20), holding the blade (20) around the handle (10).

Figure 10:
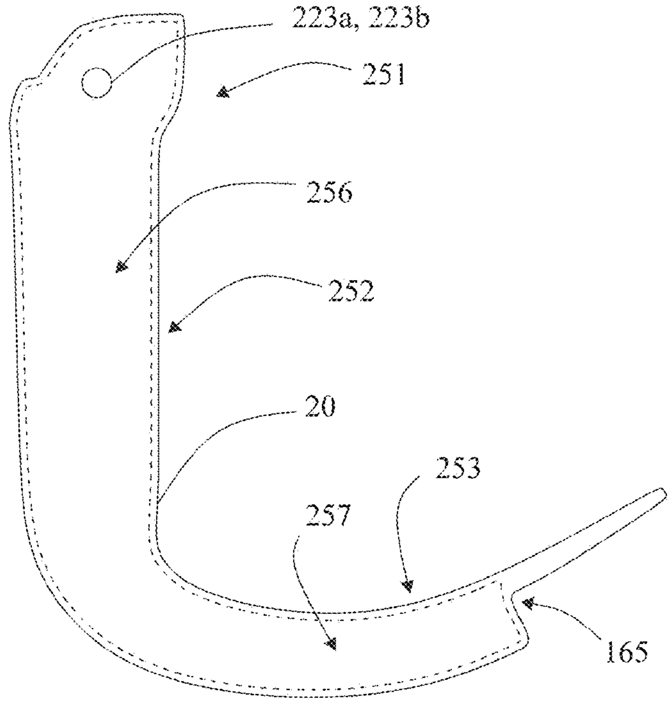
FIG. 10 illustrate a side view of the blade of the video laryngoscope in accordance with the present invention.

Referring now to FIG. 10, the blade (20) includes an attaching portion (251), a gripping portion (252), and a tongue portion (253). The attaching portion (251) is at the proximal end of the blade (20) and is adapted to attach the blade (20) to the handle (10). The attaching portion (251) includes at least two openings (223*a*, 223*b*) positioned to engage with the two ball projections (211*a*, 211*b*) of the handle (10). The two openings (223*a*, 223*b*) are provided to engage with the corresponding two ball projections (211*a*, 211*b*) during the intubation process. The attachment mechanism (21) allows the detachment of the handle (10) by pressing the two ball projections (211*a*, 211*b*) inward. The blade (20) has a first cavity (256) formed at the attaching portion (251) and the gripping portion (252) of the blade (20). The first cavity (256) is having a shape that is adapted to fit over the handle (10) and cover the handle (10) during the intubation process. The first cavity (256) allows the blade (20) to accommodate the handle (10) and remain firm in place during the intubation process. The first cavity (256) is formed at the attaching portion (251) and extends through the gripping portion (252).

The gripping portion (252) is a middle section of the blade and is arranged between the attaching portion (251) and the tongue portion (253). The gripping portion (252) is configured to provide a grip for the clinician during the intubation process. The gripping portion (252) has indentations (not shown) or other surface textures on the outer surface of the gripping portion (252) to enhance the grip of the clinician.

Furthermore, the tongue portion (253) is a distal end of the blade (20) located after the gripping portion (252). The tongue portion (253) is provided to interact with the patient's anatomy, particularly during intubation. In the present embodiment, the tongue portion (253) is an integral part of the blade (20) and transversally extends from the gripping portion (252). The tongue portion (253) is configured to receive the camera channel (15) and the camera housing (16). The tongue portion (253) includes a camera housing opening (165) to accommodate the camera housing (16) facing outside of the blade (20) allowing an image sensor (161) arranged within the camera housing (16) to capture visuals of the patient's airway, including the endotracheal tube, larynx, and trachea.

Specifically, the blade (20) has a second cavity (257) formed at the tongue portion (253) of the blade (20). The second cavity (257) is configured to accommodate the camera channel (15) and the camera housing (16) therein. The second cavity (257) accommodates the camera channel (15), which runs along the length of the tongue portion (253). The second cavity (257) provides space for the camera channel (15) to be housed within the blade (20). Further, the camera housing (16) is exposed through the camera housing opening (165) arranged in the tongue portion (253) to allow the image sensor (161) to capture the visuals of the patient's airway.

After the intubation process, the blade (20) is detachable from the handle (10) by pressing the two ball projections (211*a*, 211*b*) against the biasing force exerted by the biasing members (212*a*, 212*b*). When the pressure to the two ball projections (211*a*, 211*b*) is applied, the two ball projections (211*a*, 211*b*) are pushed inward, overcoming the biasing force of the biasing members (212*a*, 212*b*) and moving toward the center of the handle (10) (as shown in FIG. 9*b*). The two ball projections (211*a*, 211*b*) are moved towards the center of the handle (10) to disengage from the corresponding openings (211*a*, 211*b*) in the blade (20), allowing the blade (20) to be detached from the handle (10). Particularly, upon pressing the two ball projections (211*a*, 211*b*), the blade (20) is slidable over the handle (10) and the camera channel (15) in a downward direction (shown in FIG. 9*c*), thereby completely removing the blade (20) from the handle (10) and disposing of it after the intubation process.

Further, the display unit (30) is placed inside the lower panel (42) of the display cover (40) and the upper panel (44) is pivoted to close the display cover (40). The flexible sheath is wrapped around the attachment assembly (25) and the portion of the handle (10). Once the flexible sheath is wrapped, the video laryngoscope (100) is ready to use for the intubation process. The display unit (30) is rotated to configure the position according to the clinician's requirement. The movement of the display unit (30) is facilitated by the hinge (26).

While performing the intubation process, the power button (32) is pressed to activate the display screen (34), the image sensor (161), and the light source (162). The visuals of the path of the endotracheal tube and the airway are displayed on the display screen (34). The deflector (18) of the camera housing (16) reduces the scattering of the light from the light source (162). The deflector (18) helps to reduce the distortion and blurriness of the images. Further, the record button (29) is provided to capture the image and record the video. The record button (29) is pressed and released to capture the image, and the record button (29) is pressed and held for 2 to 3 seconds to record the video. The video laryngoscope (100) is completely covered from the outside eliminating the risk of the video laryngoscope (100) getting infected. After the intubation process, the display cover (40) is removed from the display unit (30) and disposed of to avoid spreading infection. Further, the blade (20) is removed from the handle (10). The blade (20) which is mainly in contact with the body parts is disposed of after one use which helps to reduce the rate of infection or cross-contamination spread due to the repetitive use of the blade (20).

Further, the video laryngoscope (100) allows the clinician to have one hand free while operating the video laryngoscope (100) during the intubation process. In an operating room, clinicians need free hands to simultaneously use multiple devices or perform multiple actions. With the placement of the power button (32) at the bottom left of the display unit (30), the menu icon on the bottom left of the display screen (34) and the record button (29) under the display unit (30), the clinician can fully operate the video laryngoscope (100) with their left hand thus leaving the right hand free.

In another aspect of the present invention, the video laryngoscope (100) includes a handle (10), a blade (20), and a display unit (30). The display unit (30) is attached to the handle (10) without using an attachment assembly (25). Specifically, the display unit (30) includes an attaching element (not shown) extending from a bottom portion of the display unit (30) to attach with the handle (10). It is obvious to a person skilled in the art to configure the attaching element of the display unit (30) to provide a threaded attachment or a snap-fit attachment or a similar attachment, to ensure a secure and functional connection between the display unit (30) and the handle (10).

Therefore, the present invention has the advantage of providing the video laryngoscope (100) to perform the intubation process. The video laryngoscope (100) is provided with the display unit (30) which rotates and moves in the back-and-forth direction to increase the visibility for the clinician. Further, the handle (10) of the video laryngoscope (100) is adapted to receive the adult blades as well as child blades, which reduces the other requirements like different handles for different blades or mountings to receive the different types of blades on the same handle (10). Further, the deflector (18) reduces the distortion and blurriness of the images for better quality visualisation. Furthermore, the handle (10) is covered by the blade (20) and the display unit (30) is covered by the display cover (40) which completely covers the video laryngoscope (100) and prevents the video laryngoscope (100) from getting infected during the intubation process.

The foregoing descriptions of specific embodiments of the present invention have been presented for purposes of illustration and description. They are not intended to be exhaustive or to limit the present invention to the precise forms disclosed, and obviously, many modifications and variations are possible in light of the above teaching. The embodiments were chosen and described in order to explain the principles of the present invention best and its practical application, to thereby enable others skilled in the art to best utilise the present invention and various embodiments with various modifications as are suited to the particular use contemplated. It is understood that various omission and substitutions of equivalents are contemplated as circumstance may suggest or render expedient, but such are intended to cover the application or implementation without departing from the scope of the claims of the present invention.

I claim:

1. A video laryngoscope (100) comprising:

a handle (10) configured to facilitate gripping during intubation;

a camera channel (15) extending along the handle (10);

a blade (20) configured to slide over and cover the handle (10) and the camera channel (15), wherein the blade (20) is detachable from the handle (10) after an intubation process;

a camera housing (16) arranged at a lower end of the handle (10), the camera housing (16) including an image sensor (161) and a light source (162);

a deflector (18) positioned between the image sensor (161) and the light source (162) to minimize light scatter and enhance image quality, wherein the deflector (18) is detachable and replaceable;

a display unit (30) removably attached to the handle (10) using a hinge mechanism (26) that allows for adjustable viewing angles; and an attachment assembly (25) connecting the display unit (30) to the handle (10), the attachment assembly (25) includes a quick-connect and release mechanism facilitated by radially biased ball projections (271*a*, 271*b*), wherein the display unit (30) is adapted to automatically adjust an orientation of a displayed image when the display unit (30) is rotated, facilitating clear viewing in various procedural positions.

2. The video laryngoscope (100) as claimed in claim 1, wherein the display unit (30) includes a user-accessible record button (29) on a housing (27) of the attachment assembly (25), enabling clinicians to capture images and videos during use.

3. The video laryngoscope (100) as claimed in claim 1, wherein a housing (27) of the attachment assembly (25) integrates automatic electrical connectivity with the handle (10), wherein electrical connectors within the attachment assembly (25) automatically establish a connection upon aligning and attaching the display unit (30) to the handle (10).

4. The video laryngoscope (100) as claimed in claim 1, wherein the display unit (30) includes an output port (33), enabling connection to external displays for broader visual access during procedures.

5. The video laryngoscope (100) as claimed in claim 1, wherein the ball projections (271*a*, 271*b*) of the attachment assembly (25) are mechanically biased to extend and retract for securing the display unit (30) in place or releasing it for detachment.

6. The video laryngoscope (100) as claimed in claim 1, further comprising a display cover (40) that wraps around both the display unit (30) and attachment assembly (25), maintaining sterility throughout the intubation process.

7. The video laryngoscope (100) as claimed in claim 1, wherein the handle (10) includes an attachment mechanism (21) comprising two radially biased ball projections (211*a*, 211*b*) arranged opposite to each other to provides a secure and quickly detachable connection for various blade types.

8. The video laryngoscope (100) as claimed in claim 7, wherein the blade (20) is attachable to the handle (10) via the attachment mechanism (21), comprising two radially biased ball projections (211*a*, 211*b*) that extend from a center axis of the handle (10) to securely engage with corresponding openings (223*a*, 223*b*) in the blade (20), the attachment mechanism (21) is adapted to securely hold the blade (20) in place during intubation, and can be pressed to release the blade (20) for detachment after the procedure.

9. The video laryngoscope (100) as claimed in claim 1, wherein the blade (20) is slidable over the camera channel (15) to facilitate attachment and detachment without disrupting the visual transmission of the image sensor (161).

10. The video laryngoscope (100) as claimed in claim 1, includes a touchscreen interface on the display unit (30) for interactive control over device settings, stored data access, and operational adjustments.

11. The video laryngoscope (100) as claimed in claim 1, wherein the display unit (30) further comprises an automatic image orientation correction feature (30*a*) configured to adjust the displayed image to a standard upright orientation when the display unit (30) is rotated by approximately 180 degrees, facilitating improved usability during procedures involving patients with elevated body mass index.

12. The video laryngoscope (100) as claimed in claim 11, wherein the display unit (30) is further configured to permit manual override of the image orientation correction feature (30*a*) by user input, including swiping gestures on a display screen (34) or pressing a designated button on the display unit (30).

13. The video laryngoscope (100) as claimed in claim 1, wherein the hinge mechanism (26) connecting the display unit (30) to a housing (27) of the attachment assembly (25) is configured to allow 360-degree movement of the display unit (30) relative to the housing (27), and further includes predetermined stop positions at specific angles for optimal viewing, with automatic image orientation correction at each stop to maintain proper display alignment.

14. The video laryngoscope (100) as claimed in claim 1, wherein the display unit (30) further comprises password-protected access to stored visual data, requiring a user-defined password to access the stored video files or to connect the video laryngoscope (100) to external computing devices, including personal computers, tablets, and similar devices.

15. The video laryngoscope (100) as claimed in claim 14, wherein the display unit (30) includes a default password, wherein the password is configurable by the user to a six-digit combination, thereby enhancing security for patient data protection.

16. A video laryngoscope (100) comprising:

a handle (10) with integrated visual transmission capabilities through a camera channel (15);

a blade (20) configured to slide over and cover the handle (10) and the camera channel (15), wherein the blade (20) is detachable from the handle (10) after an intubation process, and wherein the blade (20) is slidable over the camera channel (15) to facilitate attachment and detachment without disrupting the visual transmission of the image sensor (161);

a camera housing (16) within the camera channel (15) that includes a light source (162) and an image sensor (161);

a light-absorbing deflector (18) positioned between the light source (162) and the image sensor (161) to reduce glare, wherein the deflector (18) is detachable and replaceable;

a display unit (30) that attaches to the handle (10) and is capable of rotating via a hinge (26) to provide optimal viewing angles;

a connection system between the handle (10) and the display unit (30) that includes a housing (27) with electrical connectors for instant visual feedback on the display unit (30);

and a security feature enabling encryption and password protection for accessing saved images and videos on the video laryngoscope.

17. The video laryngoscope (100) as claimed in claim 16, wherein the hinge (26) is configured to allow 360-degree movement of the display unit (30) relative to the handle (10), and further includes predetermined stops at specific angles for optimal viewing, with automatic image orientation correction at each stop to maintain proper display alignment.

18. The video laryngoscope (100) as claimed in claim 16, wherein the security feature further protects the device's connectivity, preventing unauthorized access or data transfer during or after intubation procedures.

* * * * *